US008967537B2

(12) United States Patent
Rittner et al.

(10) Patent No.: US 8,967,537 B2
(45) Date of Patent: Mar. 3, 2015

(54) OXYGEN BREATHING DEVICE WITH REDUNDANT SIGNAL TRANSMISSION

(75) Inventors: Wolfgang Rittner, Siblin (DE); Rudiger Meckes, Berkenthin (DE); Peter Glosekotter, Steinfurt (DE); Christoph Bauer, Ibbenburen (DE)

(73) Assignee: Zodiac Aerotechnics, Plaisir (FR)

( * ) Notice: Subject to any disclaimer, the term of this patent is extended or adjusted under 35 U.S.C. 154(b) by 71 days.

(21) Appl. No.: 13/606,076

(22) Filed: Sep. 7, 2012

(65) Prior Publication Data

US 2013/0037029 A1 Feb. 14, 2013

Related U.S. Application Data

(62) Division of application No. 12/538,185, filed on Aug. 10, 2009, now Pat. No. 8,261,744.

(60) Provisional application No. 61/100,290, filed on Sep. 26, 2008.

(51) Int. Cl.

| | |
|---|---|
| ***B64D 11/00*** | (2006.01) |
| ***A61M 16/00*** | (2006.01) |
| ***A62B 7/14*** | (2006.01) |
| ***A62B 9/00*** | (2006.01) |
| *A62B 7/02* | (2006.01) |
| *A62B 7/08* | (2006.01) |

(52) U.S. Cl.

CPC ... *A62B 7/14* (2013.01); *A62B 9/00* (2013.01); *A62B 7/02* (2013.01); *A62B 7/08* (2013.01)

USPC ..................... 244/118.5; 128/204.29; 29/428; 29/407.04

(58) Field of Classification Search

USPC ........ 244/118.5; 128/201.21–202.11, 204.13, 128/204.21, 204.209, 206.21, 128/206.27–206.28, 204.29; 454/71–74; 29/428, 407.04

See application file for complete search history.

(56) References Cited

U.S. PATENT DOCUMENTS

| | | | | | |
|---|---|---|---|---|---|
| 2,934,293 | A | * | 4/1960 | Boehme et al. | 244/118.5 |
| 4,651,728 | A | * | 3/1987 | Gupta et al. | 128/201.28 |
| 5,738,092 | A | * | 4/1998 | Mock et al. | 128/205.23 |
| 5,809,999 | A | * | 9/1998 | Lang | 128/200.24 |

(Continued)

FOREIGN PATENT DOCUMENTS

| | | |
|---|---|---|
| EP | 0402045 | 12/1990 |
| GB | 2127902 | 4/1984 |

(Continued)

*Primary Examiner* — Tien Dinh
*Assistant Examiner* — Assres H Woldemaryam
(74) *Attorney, Agent, or Firm* — Kilpatrick Townsend & Stockton LLP; Dean W. Russell; Renae Bailey Wainwright

(57) ABSTRACT

The invention relates to an arrangement of a plurality of oxygen breathing devices, in particular for providing oxygen to passenger or crew of an aircraft, each oxygen breathing device comprising an oxygen source, wherein oxygen is stored, in particular in chemically bound form or compressed form, an oxygen guiding device for guiding oxygen from the oxygen source to a person. According to the invention, an arrangement of a plurality of oxygen breathing devices is provided, wherein a first one of said plurality of oxygen breathing devices further comprises an integrated transmitter comprising a sender adapted for wireless communication with a receiver of a second one of said oxygen breathing devices and a receiver adapted for wireless communication with a sender of said second oxygen breathing device.

3 Claims, 2 Drawing Sheets

(56) References Cited

U.S. PATENT DOCUMENTS

| | | | | |
|---|---|---|---|---|
| 6,121,881 | A * | 9/2000 | Bieback et al. | 340/573.1 |
| 6,244,540 | B1 * | 6/2001 | Stabile et al. | 244/118.5 |
| 6,935,593 | B2 * | 8/2005 | Meckes et al. | 244/118.5 |
| 7,784,462 | B2 * | 8/2010 | Vogt et al. | 128/204.29 |
| 7,871,038 | B2 * | 1/2011 | Space et al. | 244/118.5 |
| 2007/0057122 | A1 * | 3/2007 | Lee et al. | 244/118.5 |
| 2007/0057785 | A1 * | 3/2007 | Lee | 340/541 |
| 2007/0068520 | A1 * | 3/2007 | Laib et al. | 128/201.19 |
| 2007/0144597 | A1 * | 6/2007 | Cazenave et al. | 137/899.2 |
| 2008/0053541 | A1 * | 3/2008 | Meckes et al. | 137/624.27 |
| 2010/0096919 | A1 * | 4/2010 | Meckes et al. | 307/9.1 |

FOREIGN PATENT DOCUMENTS

| | | |
|---|---|---|
| JP | 10066323 | 3/1998 |
| WO | WO 2007/140948 | 12/2007 |

* cited by examiner

OXYGEN BREATHING DEVICE WITH REDUNDANT SIGNAL TRANSMISSION

CROSS-REFERENCE TO RELATED APPLICATIONS

This application is a divisional application of U.S. Ser. No. 12/538,185 filed on Aug. 10, 2009, which claims the benefit of U.S. Provisional Application No. 61/100,290 filed on Sep. 26, 2008, the contents of both of which are incorporated herein by reference.

BACKGROUND OF THE INVENTION

The invention relates to an arrangement of a plurality of oxygen breathing devices, in particular for providing oxygen to passenger or crew of an aircraft, each oxygen breathing device comprising an oxygen source, wherein oxygen is stored, in particular in chemically bound form or compressed form, an oxygen guiding device for guiding oxygen from the oxygen source to a person. A further aspect of the invention is an oxygen breathing device and a method for installing an emergency oxygen supply arrangement in an aircraft and a method of providing oxygen to passengers of an aircraft.

Arrangements of such oxygen breathing devices of the aforementioned type are used for a number of purposes where temporary or permanent supply of oxygen to a human person is necessary. A particular field of application of such oxygen breathing devices is the field of aircraft, wherein a pressure drop within an aircraft flying at high altitude may make it necessary to supply the passengers and the crew members with oxygen. Usually, an oxygen breathing device is provided for each crew member and passenger or a group thereof and is usually arranged above the passenger. In case of an emergency, such oxygen breathing device is activated, for example automatically by a cabin pressure monitoring system or manually by a crew member, whereafter an oxygen mask connected via a hose to an oxygen source falls from above the passenger downwards and can be used by the passenger. The flow of oxygen may be started automatically by activation of the system by the crew member or may be activated by a particular action undertaken by the passenger, e.g. by pulling the mask towards himself to thus activate the device by a pulling force transferred via the hose guiding the oxygen flow or an additional lanyard coupled to the oxygen mask.

A general problem associated with modern aircraft is the desire to provide an overall lightweight construction of the aircraft to reduce fuel consumption of the aircraft. It is to be understood that such lightweight construction may comprise a reduction of weight of structural components like wings of the aircraft but may also comprise a reduction of the weight of cabin interior elements, including passenger service units (PSU) and the like. It is an object of the invention to provide an oxygen breathing device allowing such lightweight construction of modern aircraft.

A still further object in design of modern aircraft is to allow efficient manufacturing and maintenance of the aircraft to reduce manufacturing and maintenance costs. It is an object of the invention to provide an oxygen breathing device allowing such reduced manufacturing and maintenance costs.

A particular problem associated with such oxygen breathing devices is the need to control the pressure and/or the flow of the oxygen provided to the person. If too little oxygen is provided to the person, this may cause severe damages to the person. Providing too much oxygen will require a large storage mass of the oxygen source and thus increase the total weight. Thus, usually a control unit is provided to control the flow and/or pressure of the oxygen. Such control unit may control the flow and/or pressure depending on the ambient pressure, the ambient oxygen content, the withdrawal of oxygen by the passenger or other input parameters.

Generally, it is known to drive such control unit using a drive energy supplied from an external energy source, in particular from the energy supply system of an aircraft in case where the oxygen breathing device is installed in such an aircraft. However, such approach of energy supply results in the need of extensive wiring and thus increased weight. Further, such wiring requires increased manufacturing efforts and thus tends to increase the manufacturing costs of aircraft.

A still further problem associated with such oxygen breathing devices lies in the fact that in modern aircraft a high variety of interior design is desired. This results in the need for interior cabin elements like oxygen breathing devices or passenger units which are adapted to be implemented into the aircraft at different locations and in different numbers. Further, it is desirable that the aircraft may be modified later without substantial constructive work in case that the interior design is changed. Prior art oxygen breathing devices require intensive preparational design work, commissioning, isolation and installation in the course of the initial manufacturing as well as later modification of an aircraft.

Still further it is a need for vital functions of an aircraft to provide safety against failure of single components. Often, this is achieved by redundant provision of such components which, however, further increases the weight, installation efforts and costs of systems providing such vital functions.

SUMMARY OF THE INVENTION

The invention aims to provide an oxygen breathing device which overcomes at least some of the aforementioned drawbacks and provides better safety to a person supplied by the oxygen breathing device, in particular in case of a severe emergency situation.

According to a first aspect of the invention, this object is achieved by providing an arrangement of a plurality of oxygen breathing devices as described beforehand, wherein a first one of said plurality of oxygen breathing devices further comprises an integrated transmitter comprising a sender adapted for wireless communication with a receiver of a second one of said oxygen breathing devices and a receiver adapted for wireless communication with a sender of said second oxygen breathing device, wherein said second oxygen breathing device is arranged in a distance from the first oxygen breathing device, wherein the sender and receiver of said integrated transmitter are adapted to receive and send at least a decompression signal signalising the need to activate oxygen supply from said oxygen source via said oxygen guiding device, and wherein preferably said transmitter is connected to said oxygen source to activate oxygen supply via said oxygen guiding device upon receipt of such decompression signal.

According to this aspect of the invention, an oxygen breathing device is provided which allows to omit specific wiring required for signal transmission to each particular oxygen breathing device. Instead, a wireless signal transmission is provided by respective transmitters associated to a first and second oxygen breathing device. It is to be understood that the invention may be implemented in an arrangement having a plurality of oxygen breathing devices in such a way that only single oxygen breathing devices are associated with a respective transmitter and signal transmission between other oxygen breathing devices may be accomplished in a conventional way via respective wiring. Preferably, each oxygen breathing device is associated to a respective transmitter such that no wiring for signal transmission is required at all.

According to the invention, the transmitter is not only adapted to receive such signal but further to send such signal to another transmitter. This allows to build up a wireless network comprising a plurality of nodes inside the aircraft wherein each node is capable of receiving and sending signals like an emergency decompression signal. This is of particular relevance since in such wireless network failure of one single node can easily be compensated by transmitting the signals via different nodes and will thus not negatively affect the performance of the whole system. Thus, failure of one single oxygen breathing device or its associated transmitter may in the worst case result in failure of said single oxygen breathing device but will not result in failure in signal transmission to other oxygen breathing devices and thus allow the remaining oxygen breathing devices to function properly.

It is to be understood that the sender of the first or second oxygen breathing device may be used to forward a decompression signal which is received by the receiver beforehand or may send a decompression signal which was generated inside the first or second oxygen breathing device, respectively, like e.g. by a respective pressure sensor integrated into the oxygen breathing device. In the arrangement, a central pressure sensor associated with a transmitter comprising at least a sender may be provided for initiating the sending of a decompression signal to at least one oxygen breathing device.

According to a first preferred embodiment, said first oxygen breathing device further comprises a control unit adapted to monitor a wireless communication path between said integrated transmitter and a transmitter of said second oxygen breathing device, wherein said control unit is further adapted to detect partial or total failure of said wireless communication path and to switch to a wireless communication between said integrated transmitter and another transmitter, preferably a transmitter of a third oxygen breathing device in case of such failure.

According to this embodiment, a set-up of the arrangement is provided which is safe against failure of a single communication path between a first and a second oxygen breathing device. This is achieved by providing the option to transmit said decompression signals via a different transmitter which may be incorporated into a different oxygen breathing device. In such case, the first oxygen breathing device may automatically switch from a signal transmission with a second oxygen breathing device to a signal transmission with a third oxygen breathing device in case that the monitoring of the communication with the second oxygen breathing device reveals failure of said connection. It is to be understood that it is particularly preferred that each oxygen breathing device monitors its present wireless communication path and in case of failure of said present wireless communication path switches to a different wireless communication path which may be provided via another node of the whole arrangement, like e.g. via a transmitter incorporated into another oxygen breathing device or an isolated transmitted incorporated into the arrangement.

According to a further preferred embodiment said first oxygen breathing device further comprises a control unit adapted to automatically detect a presence of another transmitter, in particular said transmitter of said second oxygen breathing device and to establish wireless connection between said integrated transmitter and said other transmitter. This preferred embodiment will allow a self-configuring and maintaining of the wireless connectivity of the oxygen breathing device included into the arrangement according to the invention. Still further, this preferred embodiment will allow self-deployment of the whole system and thus significantly speed up the installation and deployment of the whole arrangement. This is achieved by an automatic deployment of the wireless communication of each single node of the arrangement, wherein such node may comprise an oxygen breathing device comprising a transmitter or an isolated transmitter incorporated into this arrangement. Further, this preferred embodiment will allow easy extension of the arrangement, since in case that further oxygen breathing devices are to be incorporated into the arrangement, such oxygen breathing devices will only have to be installed at their location inside the aircraft cabin and to be activated and will then deploy themselves and establish the wireless communication within the arrangement required for proper functioning.

Still further, it is preferred that the arrangement according to the invention comprises a plurality of oxygen breathing devices, wherein each oxygen breathing device comprises an integrated transmitter for wireless communication with another transmitter of another oxygen breathing device and wherein preferably each oxygen breathing device comprises a control unit. Such set-up of the arrangement will allow to design a network having different sizes and numbers of nodes and to establish point to multipoint networks, wherein signals converge at a single endpoint or mesh network offering multiple redundant communication paths throughout the network or any combination of these two protocols. This will allow to provide properties like self-configuring and maintaining connectivity, distributed sensing of environmental data if further respective sensors are implemented at one or more of the nodes, i.e. the oxygen breathing devices, distributed computation capabilities and a bandwidth and resources which scale with the network size.

According to a further preferred embodiment, said arrangement may comprise one or more isolated transmitter units adapted to wirelessly receive a decompression signal and to wirelessly transmit said decompression signal to another transmitter. This will allow to increase the number of nodes inside the wireless communication network without increasing the number of oxygen breathing devices and will thus result in a higher degree of redundant communication paths within the whole arrangement. The additional isolated transmitter units may be used as central distribution nodes each being arranged in a sector comprising a group of oxygen breathing devices and each being arranged in a certain distance from another isolated transmitter unit.

According to a further preferred embodiment, the arrangement may further comprise a pressure sensor and a control unit adapted to receive a pressure signal from said pressure sensor and including a comparator adapted to compare said pressure signal to a predetermined pressure range, wherein said control unit is coupled to a transmitter to send said decompression signal to at least one transmitter of an oxygen breathing device, wherein said pressure sensor is preferably integrated into one of said oxygen breathing devices. According to this preferred embodiment, a pressure sensor for detecting ambient pressure like e.g. inside an aircraft cabin is provided and directly coupled to a transmitter unit for sending an emergency decompression signal to at least one oxygen breathing device inside the arrangement. This will allow to automatically provide oxygen masks to the passengers and/or to activate oxygen supply by wireless transmission of said decompression signal and without the need for manual activation by a crew member or the like. It is particularly preferred to include such sensor in one or more of the oxygen breathing devices comprised in the arrangement which will allow to provide redundant detection of a decompression situation at different locations inside an aircraft cabin.

Still further, it is preferred that each oxygen breathing device comprises a light sensitive element coupled to said integrated transmitter of the respective oxygen breathing device, wherein said light sensitive element is adapted to send a signal to said transmitter if a light event is detected and wherein said transmitter is adapted to send a light event reception signal in case of receipt of such signal from the light sensitive element. Such preferred embodiment will allow to localize an oxygen breathing device when installed and to facilitate the search for such oxygen breathing device in case of failure. In detail, the location of the oxygen breathing device may be registered by sending a light signal to the light sensitive element in a known direction from a known point of origin and to associate the light event reception signal to said particular oxygen breathing device which is subjected to said light event with a particular location which is to be calculated from the point of origin of the light event and the direction. In this context it is to be noted that it is not required to direct the light event along a single line but the location of an oxygen breathing device via such light event may be accomplished by providing a light event in a specific section, along a specific stripe or the like.

According to a further preferred embodiment, the arrangement according to the invention may be further improved by a locating device comprising a position sensor to determine its position in space and a light source for emitting light in a certain direction or sector, said locating device further comprising a receiver adapted to receive said light event reception signal from a transmitter coupled to a light sensitive element having received light from said light source and a control unit and a memory adapted to register and store at least a coordinate of the location of said light sensitive element, preferably the exact location of said light sensitive element. According to this preferred embodiment, a locating device is provided for detecting the position of light-sensitive elements associated with oxygen breathing devices. It is to be understood that such locating device may comprise a module which allows exact determination of the position of the position detection device itself, be it in absolute coordination like e.g. by a GPS module or in relation to a fixed reference point within a space like a cabin of an aircraft. By such determination of the position of the locating device it is further possible to determine the location of a light-sensitive element which is arranged in a certain direction or distance from said locating device. Said direction or distance may be determined by emitting light in said certain direction, whereby it is to be understood that the light may be emitted in a certain section or structure or the like. It is further to be understood that only a coordinate may be determined and stored within the locating device to allow a calculation of the position of said light-sensitive element by combining two or more measurements revealing respective two or more such coordinates. This allows to determine the exact location of the light-sensitive element by way of a cross-bearing process.

It is important to notice according to this preferred embodiment that only one locating device comprising a plurality of specific modules is required for detecting the position of all light-sensitive elements which are provided within a network of a plurality of oxygen breathing devices comprising such light-sensitive element. Thus, such a locating device may only be required for initial set-up of said network to register the position of each single oxygen breathing device having such light-sensitive element. Hereafter, the locating device may be removed and be used for initial set-up in another network, since only the data stored in said initial process is required for maintenance and service of the network.

According to a second aspect of the invention, an oxygen breathing device, in particular for providing oxygen to passenger or crew member of an aircraft is provided, the device comprising an oxygen source, wherein oxygen is stored, in particular in chemically bound form or compressed form, an oxygen guiding device for guiding oxygen from the oxygen source to a person, which is characterized by an integrated transmitter comprising

- a sender adapted for wireless communication with another receiver and
- a receiver adapted for wireless communication with another sender, wherein the sender and receiver of said integrated transmitter are adapted to receive and send at least a decompression signal signalising the need to activate oxygen supply from said oxygen source via said oxygen guiding device, and wherein said transmitter is preferably connected to said oxygen source to activate oxygen supply via said oxygen guiding device upon receipt of such decompression signal.

Such oxygen breathing device corresponds to a single oxygen breathing device and arrangement as described above and is particularly well-adapted for building up such an arrangement comprising a plurality of oxygen breathing devices. Further, such oxygen breathing device may be used to reconfigure or extend such an arrangement by replacing or adding such oxygen breathing devices.

It is particularly preferred that said oxygen breathing device comprises a control unit for controlling pressure and/or flow rate of the oxygen flowing through the guiding device and an energy conversion and supply device which is adapted to convert energy stored or produced within the oxygen breathing device into an energy required by the control unit, and provide said energy required by the control unit to the control unit.

According to this preferred embodiment, the control unit is at least particularly provided with drive energy which is generated by converting energy stored or produced within the oxygen breathing device itself. Generally a number of possibilities are available to store or produce such energy within the device itself like pressure, thermal energy, vibration, photovoltaics or acoustics. In particular, the energy may be stored in the form of pressurized oxygen, whereby the pressure itself is converted into the drive energy by relaxation. Alternatively, the energy may be stored within the device in the form of one or more chemical substances which may undergo a chemical reaction or react with each other and provide energy by such chemical reaction. For example, such chemical reaction may be exothermic and thus provide thermal energy which can be converted into drive energy of the control unit via a variety of converting methods. Still further, oscillatory motion of the oxygen breathing device itself or parts of it, e.g. induced by vibration during flight of an aircraft or the like may be converted into the drive energy of the control unit. According to a still further embodiment, the energy conversion and supply device may be adapted to convert acoustic pressure into electrical energy required by the control unit. The acoustic pressure may preferably result from sources like turbines of an aircraft or from wind-flow around an aircraft. Alternatively, other harvesting techniques may be applied, such as solar cells or piezoelectronic devices.

An important advantage of this embodiment is that the oxygen breathing device may particularly or completely supply drive energy to the control unit from internally generated energy, thus avoiding or at least reducing the danger of breakdown of the control unit following breakdown of the onboard energy supply system of an aircraft. A second advantage of the oxygen breathing device according to the invention is that it is even independent from an auxiliary emergency energy supply system of such an aircraft and may thus be driven completely independent from such energy systems. By this, an independent oxygen breathing device can be provided to increase life safety for the person supplied by the oxygen breathing device.

A second advantage of the oxygen breathing device according to this preferred embodiment is that it does not require an energy supply connection to the energy supply system of an aircraft. This makes it possible to completely omit any connecting elements or wiring since energy generation can be done in a self-sustaining manner inside each single oxygen breathing device and signal transmission is done via wireless communication. This may save weight of the overall aircraft and will further ease manufacturing of the aircraft since an independent, isolated oxygen breathing device only has to be installed close to each person inside an aircraft which shall be provided with oxygen in case of emergency but no extensive wiring or the like is required for such system. It is to be understood that the drive energy which is generated by converting energy stored or produced within the oxygen breathing device itself may further be used to supply the transmitter and any further control device or unit implemented into the oxygen breathing device with the energy required for its operation.

This preferred embodiment can be designed and further improved as described in European patent application EP 08 151 305.3 which disclosure is incorporated by reference.

In particular, it is preferred that said oxygen source is a chemical oxygen source comprising at least one or two components, said component(s) producing oxygen in a chemical reaction and wherein said energy conversion and supply device is adapted to convert heat energy generated by said chemical reaction the oxygen source into said energy required by the control unit to the control unit, wherein said energy conversion and supply device preferably is a peltier element in thermal contact with the oxygen source or wherein said energy conversion and supply device is adapted to convert energy produced by oscillatory motion of the oxygen breathing device or parts of it. With respect to the advantages and details of such preferred embodiment it is referred to EP 08 151 305.3 incorporated by reference.

Preferably, an energy storage device like e.g. a battery, in particular a thin film battery, or a capacitor may be provided to store energy for initial start-up of the oxygen breathing device. This particularly addresses the usual mode of operation of such devices being approx. 99% of its lifetime in stand-by mode but being required to start up in an emergency situation with high reliability. To this extent, the load condition of the energy storage may be monitored frequently and correct and/or insufficient load conditions may be signalized to a control unit via wireless communication like WLAN or the like.

According to a still further aspect of the invention, a method for installing an emergency oxygen supply arrangement into an aircraft is provided, the method comprising the steps:

installing a plurality of passenger oxygen breathing devices, each comprising a sender and a receiver for wireless communication with another sender and receiver, establishing a network among these plurality of oxygen breathing devices by self configuring and maintaining wireless connectivity between said senders and receivers, further including in said network at least one pressure signal coupled to a sender to wirelessly transmit an emergency decompression signal to at least one receiver in said network.

Said aspect of the invention provides for a fast and economic method to install oxygen supply devices for passengers and crew members in the manufacturing of an aircraft. In contrast to the installation method according to the prior art, the method according to the invention does not require commissioning and installation of any wiring but only requires installation of only the endpoint in form of the oxygen breathing devices to set up a wireless network. Further, the method allows to install and add other instruments as required without the need for expensive, disruptive cabling and labour. A further benefit of such method installing a wireless system is the ease of reconfiguration and expansion, since no expensive conduit must be moved or added in case of the need for an expansion or relocation of instruments. This is in particular preferable if a connection has to be established between high maintenance devices or units, such as a passenger service unit on an aircraft to a control panel or the like when such installations have vital function.

A particular advantage of the method according to the invention and the arrangement as described beforehand established by such method is the self-configuring nature of the such established network, thus not requiring a person to tell the network how to get a message to its destination. The network is preferably self-organizing and does not require manual configuration. It is preferably self-configuring and self-healing, adding of new components or relocating existing components more simple than in the prior art, since only a wireless node must be arranged within the network and turned on. The network will then discover the new node and automatically incorporate the node into the network without the need for a system administrator. Further, the network established by such method is self-healing in a sense that if one node goes down, the signals are sent through an alternate path by other nodes. By this, a passenger service unit or oxygen box which fails will be circumvent via other devices and the failure gets automatically reported back to a central control unit like a service centre or the like. The subtraction of one or more nodes (i.e. PSU or oxygen box) does not negatively affect the operation of the whole network, for no human intervention is required for the self-healing of the network.

With regard to redundancy of the network, the degree of such redundancy is essentially a function of the node density. Thus, the network can be deliberately over-designed simply by adding extra nodes, so that each device has two or more paths for sending data. Such extra nodes need not to be a PSU or oxygen boxes having a transmitter but could be single transmitters as a standardized unit as well. By this, the network is scalable and can handle hundreds or thousands of such nodes and since the operation of the network does not depend upon a central control point, adding multiple data collection points or gateways to other networks is conveniently achievable.

The method according to the invention may be further improved by the steps of:

positioning a locating device in a line of sight to at least one light sensitive element associated to one of said oxygen breathing devices, emitting a light event from said locating device to said light sensitive element, detecting said light event in said light sensitive element and sending a receipt signal to a sender coupled to said light sensitive element, sending a receipt signal from said sender to said locating device to register the position of said oxygen breathing device within a storage unit inside said locating device.

This method allows for easy localization of a node within the wireless network. This method employs an asymmetric architecture of the arrangement of the oxygen breathing devices in which the nodes within the network, i.e. the oxygen breathing devices, do not need cost-expensive additional hardware for localization purposes. All the sophisticated hardware and computation required for such localization is incorporated in one single external locating device. This external locating device uses a steerable (or hand-operated) light source which illuminates a light-sensitive element, i.e. a sensor, placed within a known terrain such as the aircraft cabin and associated to the oxygen breathing device. By this, after deployment and installation and self-organizing of the nodes into a network, the nodes execute a time synchronisation protocol. Hereafter, a technician, equipped with the external locating device, moves throughout the aircraft cabin and generates light events using the external locating device. The light-sensitive elements of the nodes detect the events and report back to the external locating device, e.g. through a base station, the time stamps when the events were detected. The external locating device computes the location of nodes. Thus, a good knowledge about its position and orientation as well as a line of sight between the external locating device and the light-sensitive elements are only requisite for such method of locating the nodes.

Alternatively, the wireless network on the aircraft may use connectivity information (hop by hop) as an indication of the proximity among the nodes. The hop count from beacon nodes to the nodes in the cabin network can be used to infer the distance.

According to a further aspect of the invention, a method of providing oxygen to passengers of an aircraft is provided, comprising the steps of a. sending an emergency decompression signal from a pressure sensor to a transmitter within a first oxygen breathing device via wireless communication,
b. providing oxygen masks and/or activating oxygen supply within said first oxygen breathing device,
c. sending said emergency decompression signal from said transmitter of said first oxygen breathing device to a transmitter of a second oxygen breathing device via wireless communication,
d. providing oxygen masks and/or activating oxygen supply within said second oxygen breathing device,
e. sending said emergency decompression signal from said transmitter of said second oxygen breathing device to a transmitter of a third oxygen breathing device via wireless communication,
f. providing oxygen masks and/or activating oxygen supply within said third oxygen breathing device.

This method allows for wireless signal transmission of an emergency decompression signal in case of a decompression of a cabin of an aircraft and thus allows a very safe activation of oxygen supply to the passenger of an aircraft in such emergency situation.

The method may be further improved by further comprising the steps of:

controlling the flow and/or pressure of the oxygen flow in a control unit, which is part of the oxygen breathing device, supplying drive energy to said control unit for driving said control of the flow and/or pressure, guiding said oxygen flow with said controlled flow and/or pressure to said person, converting energy stored or generated within said oxygen breathing device or parts of it into said drive energy of said control unit.

By this, a method of activating and supplying oxygen to a passenger of an aircraft is provided which does not need any transmission of energy or signals via a wiring at all and thus allows for safe and light-weight design of an oxygen supply arrangement and its operation. The energy may be converted from a temperature difference inside the oxygen breathing device, from oscillatory motion of the oxygen breathing device or parts of it or from acoustic pressure present in the oxygen breathing device.

BRIEF DESCRIPTION OF THE DRAWINGS

A preferred embodiment of the invention is described with reference to the figures.

DETAILED DESCRIPTION

Figure 1:
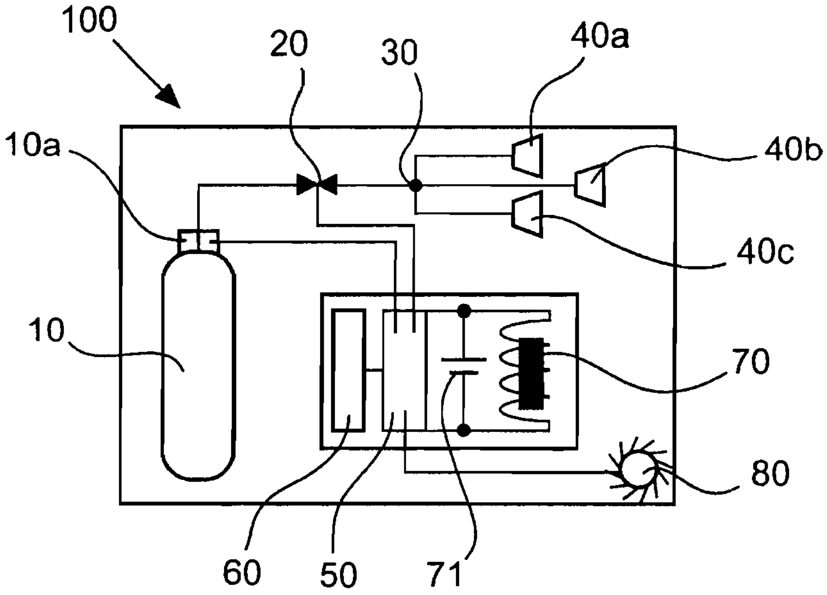
FIG. 1: shows a schematic elevational view of an oxygen breathing device according to the invention.

Referring first to FIG. 1, an oxygen breathing device 100 according to the invention comprises a chemical oxygen source 10 which is coupled in fluid communication to a flow control valve 20. A starter unit 10*a* is arranged adjacent to the chemical oxygen source 10. The starter unit 10*a* is electrically connected to a control unit 50 to receive a starting signal from said control unit 50 to thereupon activate a chemical reaction within the chemical oxygen source 10 to produce oxygen to be delivered to the flow control valve 20.

The oxygen flowing from the oxygen source 10 through the flow control valve 20 is delivered to a manifold 30 and hereafter to, for example, three passenger oxygen masks 40*a-c*.

A transmitter 60 is associated to the control unit 50 within the oxygen breathing device 1. The transmitter 60 is electrically connected to the control unit 50. The transmitter 60 is adapted to receive and send an emergency decompression signal from and to another transmitter within an aircraft cabin and to hereupon send an activation signal to the control unit 50 via the wired connection in order to release the oxygen masks 40*a-c* from the device and to start activation process of oxygen supply.

Still further, an energy conversion unit 70 is provided within said oxygen breathing device 100. Said energy conversion unit is adapted to convert oscillatory motion of the whole oxygen breathing device like e.g. resulting from vibration within the aircraft during flight and ground transfer into electrical energy. Said electrical energy may be supplied to the flow control valve 20, the control unit 50 and the transmitter 60. By this, the energy required by the control unit 50, the transmitter 60 and the flow control valve 20 is converted within the oxygen breathing device 100 and thus the oxygen breathing device is designed to be self-sustaining. A capacitor 71 is associated with said energy conversion unit 70 to store electrical energy within the oxygen breathing device. By this, the oxygen breathing device 100 is capable to start oxygen flow and control of such flow and to monitor the wireless communication of transmitter 60 even in a situation where no oscillatory motion of the oxygen breathing device 100 is present.

Still further, a light-sensitive element 80 is arranged in a corner of the oxygen breathing device 100. The light-sensitive element 80 is electrically connected to the control unit 50 to send a signal to said control unit 50 in case of reception of a light event hitting the light-sensitive element 80. The control unit 50 is adapted to send a signal to transmitter 60 to send out a light event receipt signal upon reception of a light event by said light-sensitive element 80.

Figure 2:
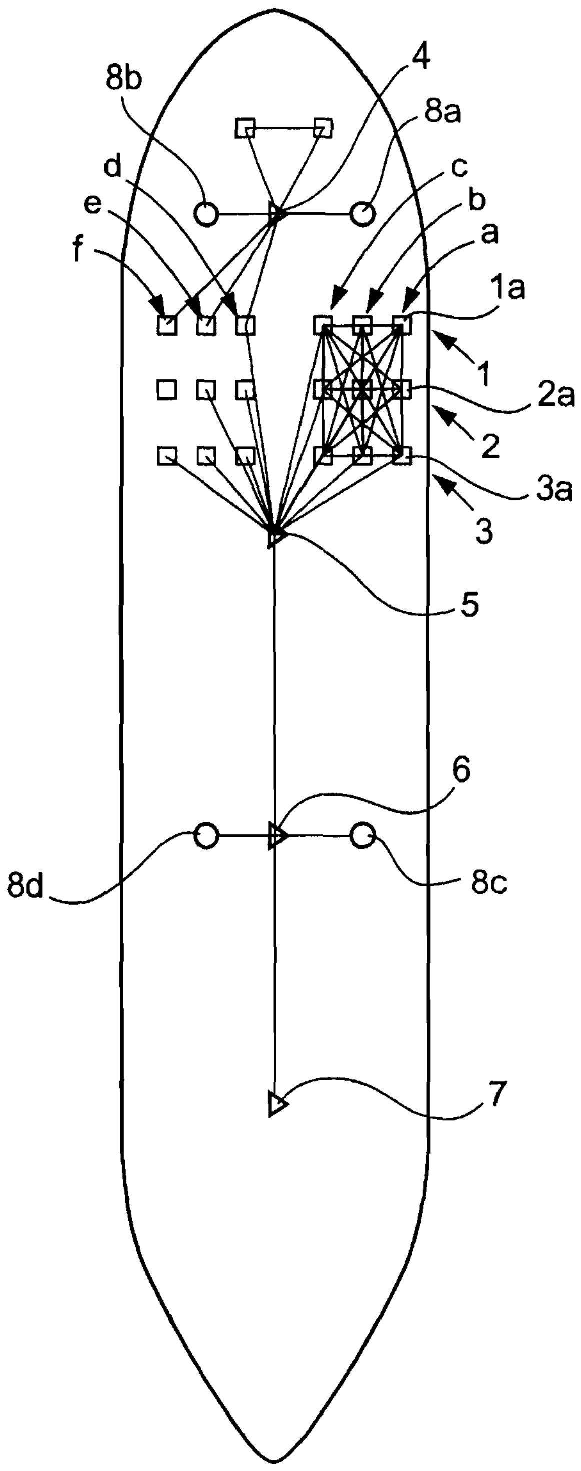
FIG. 2: shows a schematical view of an arrangement of oxygen breathing devices according to the invention.

Referring further to FIG. 2, a partial set up of a cabin interior of an aircraft is depicted. As shown, a number of oxygen breathing devices 1*a*, 2*a*, 3*a* are provided and arranged in rows 1, 2, 3 and column a-f. It is to be understood that each box in the rows 1, 2, 3 and columns a-f is provided with an oxygen breathing device although not explicitly referenced. Each oxygen breathing device is capable to deliver oxygen to a passenger sitting in vicinity to the oxygen breathing device. It is to be understood that each oxygen breathing device depicted by a square in FIG. 2 may be configured according to the oxygen breathing device 100 shown in FIG. 1.

Still further, transmitter units 4, 5, 6, 7 are distributed over the length of the aircraft cabin.

As shown by a plurality of grid lines, each transmitter arranged within an oxygen breathing device 1-3, a-f is capable to send and receive signals from any other oxygen breathing device and from any of the transmitter units 4-7. By this, a plurality of signal paths is provided for transmitting an emergency decompression signal in case of an emergency decompression to each of the oxygen breathing devices.

Still further, pressure sensors 8*a*-*d* are provided and associated with transmitters which are implemented into the network of the oxygen breathing devices and the transmitter units. By this, a decompression detected by any of the pressure sensors 8*a*-*d* may effect transmission of an emergency decompression signal via wireless communication paths between said oxygen breathing devices 1-3, a-f and said transmitter units 4-7.

Figure 3:
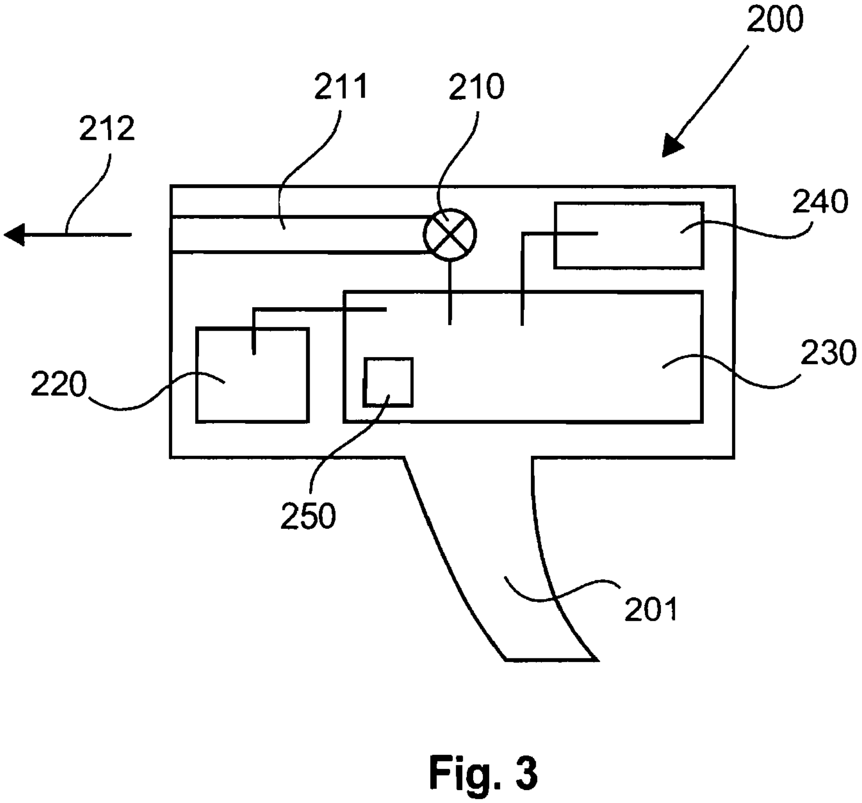
FIG. 3: shows a schematical view of a position detecting device for an arrangement of oxygen breathing devices according to the invention.

When referring to FIG. 3, an external locating device 200 is schematically depicted in a side-elevational view. The external locating device 200 comprises a handle 201 and a light source 210 which sends out light events via a channel 211 in a direction 212.

A GPS module 220 is provided for determining the absolute position of the locating device 200 and is electrically connected to a control and storage unit 230. Still further, a transmitter 240 is arranged within the locating device 200 and is electrically connected to said control and storage unit 230.

The locating device 200 allows to send out a light event via said light source 210 in a particular direction 212 to be directed to a light-sensitive element 80 of an oxygen breathing device. The position and orientation of the locating device 200 is determined by said GPS module 220 and an internal orientation sensor 250. As soon as the light event sent out via said light directing channel 211 hits upon a light-sensitive element 80, this light-sensitive element 80 will transmit a signal to its associated control unit 50 and a light event receipt signal will be transmitted from its associated transmitter 60 to the transmitter 240 of the locating device 200. By this, the position of the oxygen breathing device 100 incorporating said light-sensitive element 80 can be determined and stored within the control and storage unit 230 of the locating device 200. By this, the initial set-up of a plurality of oxygen breathing devices within an arrangement of such oxygen breathing devices in an aircraft cabin can be registered and stored for the purpose of later service and maintenance operation.

The invention claimed is:

1. A method for installing an emergency oxygen supply arrangement in an aircraft, the method comprising:

Installing a plurality of passenger oxygen breathing devices, each comprising a sender and a receiver, wherein a sender of a first passenger oxygen breathing device of the plurality of passenger oxygen breathing devices is configured to communicate with a receiver of a second passenger oxygen breathing device of the plurality of passenger oxygen breathing devices and a sender of the second passenger oxygen breathing device is configured to communicate with a receiver of the first passenger oxygen breathing device, Establishing a network among these plurality of passenger oxygen breathing devices by self configuring and maintaining wireless connectivity between said senders and receivers of the plurality of passenger oxygen breathing devices, Further including in said network at least one pressure sensor coupled to a pressure sensor sender to wirelessly transmit an emergency decompression signal to at least the receiver of the first passenger oxygen breathing device to activate oxygen supply within the first passenger oxygen breathing device.

2. The method according to claim 1 further comprising:

positioning a locating device in a line of sight to at least one light sensitive element associated to one of said plurality of passenger oxygen breathing devices, emitting a light event from said locating device to said light sensitive element, detecting said light event in said light sensitive element and sending a receipt signal to a unit coupled to said light sensitive element, wherein the unit is either the sender of the one of said plurality of passenger oxygen breathing devices or is a separate light sensitive element sender, sending a receipt signal from said unit to said locating device to register the position of said one of said plurality of passenger oxygen breathing devices within a storage unit inside said locating device.

3. The method according to claim 1 further comprising:

configuring said network so that, upon receipt of the emergency decompression signal by the receiver of the first passenger oxygen breathing device, the sender of the first passenger oxygen breathing device communicates with the receiver of the second passenger oxygen breathing device to activate oxygen supply within the second passenger oxygen breathing device.

* * * * *